United States Patent [19]

Katsunuma et al.

[11] Patent Number: 5,698,519
[45] Date of Patent: Dec. 16, 1997

[54] POLYPEPTIDE SPECIFICALLY INHIBITING CATHEPSIN L

[75] Inventors: Nobuhiko Katsunuma, Tokushima, Japan; Vito Turk, Ljubljana, Slovenia

[73] Assignee: Taiho Pharmaceutical Co., Ltd., Tokyo, Japan

[21] Appl. No.: 478,520

[22] Filed: Jun. 7, 1995

Related U.S. Application Data

[63] Continuation-in-part of PCT/JP94/01878 Nov. 8, 1994.

[30] Foreign Application Priority Data

Nov. 12, 1993 [JP] Japan ............................ 5-283270
Dec. 14, 1993 [JP] Japan ............................ 5-313533

[51] Int. Cl.$^6$ ............................ C07K 14/00; C07K 7/10; C12N 15/15
[52] U.S. Cl. ............................ 514/12; 530/350
[58] Field of Search ............................ 514/12; 530/324

[56] References Cited

FOREIGN PATENT DOCUMENTS 9108228  6/1991  WIPO.
WO 91/08228  6/1991  WIPO.

OTHER PUBLICATIONS

Lenarck et al, FEBS Letters, vol. 336 (2) 27, Dec. 1993, pp. 289–292.
FEBS Letters, vol. 336, No. 2, pp. 289–292 (1993).
Biomed. Biochim Acta 45, pp. 1375–1384 (1986).
J. Biochem, vol. 105, No. 1, pp. 143–147 (1989).
V. Turk et al. "The cystatins: protein inhibitors of cysteine proteinases", *FEBS Letters*, vol. 285 No. 2, 22 Jul. 1991, Amsterdam NL, pp. 213–219.
B. Lenarcic et al, "Pig leukocyte cysteine proteinase inhidibor (PLCPI), a new member of the stefin family", *FEBS Letters*, vol. 336, No. 2, 27 Dec. 1993, Amsterdam NL, pp. 289–292.
A. Ritonja et al, "Primary structure of a new cysteine proteinase inhibitor from pig leucocytes" *FEBS Letters*, vol. 255, No. 2, 25 Sep. 1989, Amsterdam NL, pp. 221–214.

*Primary Examiner*—Cecilia J. Tsang
*Assistant Examiner*—P. Lynn Touzeau
*Attorney, Agent, or Firm*—Sughrue, Mion, Zinn, Macpeak & Seas, PLLC

[57] ABSTRACT

The present invention provides a polypeptide having an amino acid sequence represented by Sequence No. 1 and a cathepsin L-specific inhibitor and therapeutic agent for osteoporosis comprising the polypeptide as its effective component. Since the polypeptide possesses potent inhibitory action specific to cathepsin L as well as strong bone resorption inhibitory action, the polypeptide is useful in the treatment of osteoporosis, particularly, senile osteoporosis.

5 Claims, 1 Drawing Sheet

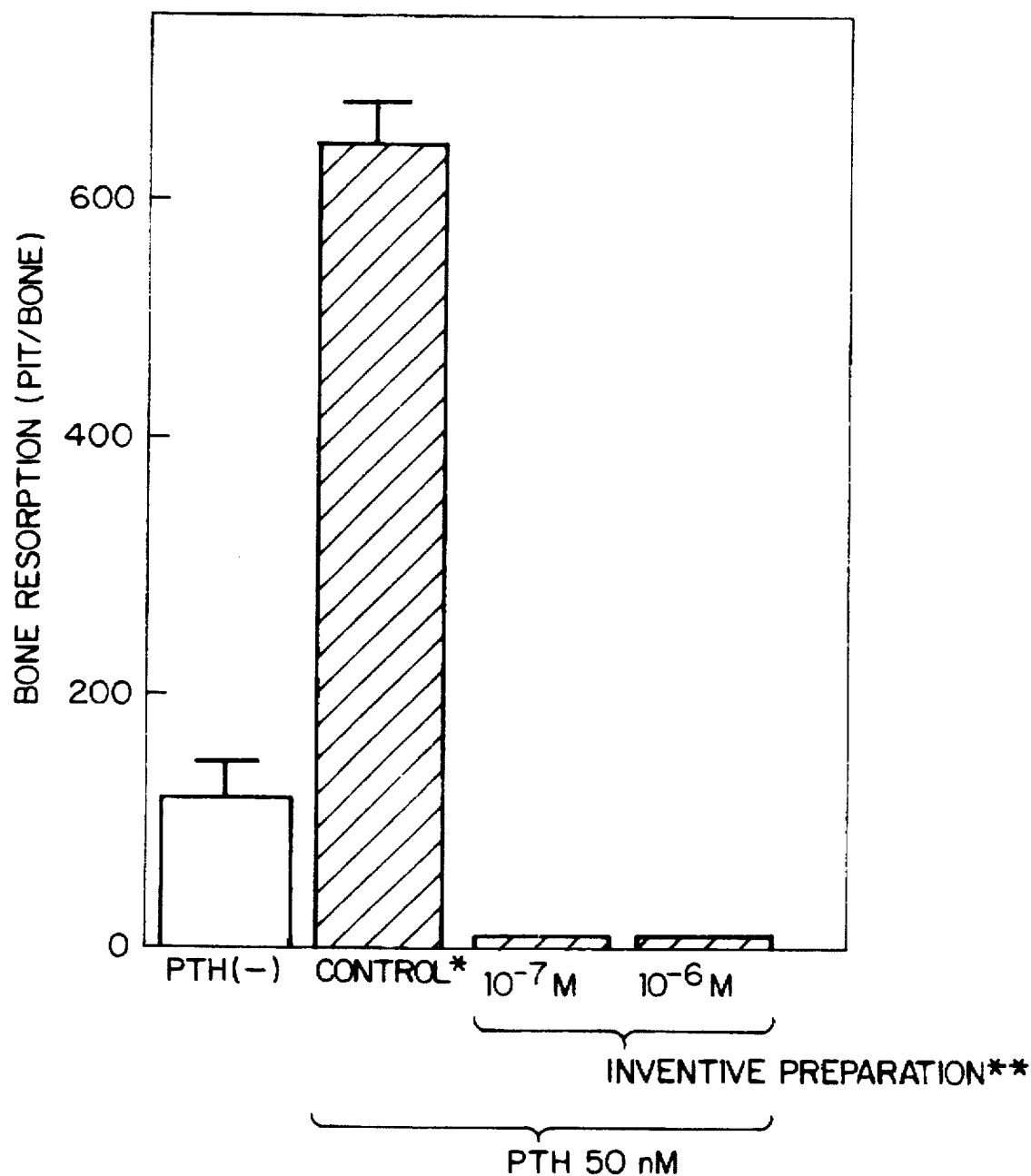

POLYPEPTIDE SPECIFICALLY INHIBITING CATHEPSIN L

CROSS REFERENCE TO RELATED APPLICATION

This is a continuation-in-part application of PCT Application No. PCT/JP94/01878 filed on Nov. 8, 1994.

TECHNICAL FIELD

The present invention relates to a novel polypeptide, and more particularly to a novel polypeptide which specifically inhibits cathepsin L and is useful as a therapeutic agent for osteoporosis.

BACKGROUND ART

In the present situation of facing the society of the aged, in other words, in the situation where the proportion of elderly citizens in the population make-up increases, abnormal exasperation of bone resorption of the elderly people becomes a serious problem because it is involved in various disabilities (curvature of the lumbar portion and the spine, articulate functional disorders, tendency of easy fracture of bones). In particular, osteoporosis has become a serious public concern. Unfortunately, there is at present no completely effective therapy for the treatment of osteoporosis.

Osteoporosis is considered to be caused by disorders of calcium deposition and abnormal degradation of collagen in supporting tissue. Vitamin $D_3$ derivatives and phosphorus-containing compounds have been studied as a countermeasure drug against the disorders of calcium deposition. Vitamin $D_3$ derivatives, however, are known to be inapplicable to senile osteoporosis, though they are effective in the growth period of bone. Phosphorus-containing compounds, on the other hand, provide only a protective action by coating the bone surface and have various adverse effects, so they are considered not to be very useful in therapy.

Calcitonin has a strong action of decreasing the serum calcium level. It is an intrinsic hormone and presents a notable transient analgesic action. It is therefore useful as a drug of immediate effect. However, it is said that bone resorption cannot be inhibited by continuous administration of calcitonin because it can be administered only by injection.

Development of drugs relying on the mechanism of abnormal exasperation of collagen degradation has just started. It has been elucidated that certain cysteine proteases, especially cathepsins, participate in collagen degradation, and several inhibitory drugs against these cathepsins have been reported (Japanese Patent Application Laid-open (kokai) Nos. SHO 63-284127 and HEI 2-218610). According to recent studies, cathepsin L, which is in the group of cathepsins (cathepsin B, cathepsin H, and cathepsin L) is known to have a remarkably strong collagen degradation action compared to other cathepsins. Experiments using test animals have revealed that inhibitory agents against cathepsin L markedly inhibit bone collagen degradation. Therefore, substances which specifically inhibit cathepsin L are said to be useful as a therapeutic agent for osteoporosis [FEB Letters, vol. 269, No. 1, p. 189–193 (1990); "Intercellular Protein Degradation", pages 118–128 (Tokyo Kagaku Dojin)].

Accordingly, an object of the present invention is to provide a novel polypeptide which is useful for the prevention and treatment of bone diseases such as osteoporosis. In more detail, the present invention provides a polypeptide which is useful for the radical prevention and treatment of osteoporosis by specifically inhibiting cathepsin L which is considered to take a major part in collagen degradation.

DISCLOSURE OF THE INVENTION

Under the above circumstances, the present inventors conducted extensive studies focusing on animal leucocytes in an attempt to obtain a cathepsin L-specific inhibitors, and as a result, they found that a novel polypeptide which has a strong cathepsin L-specific inhibiting action and bone resorption inhibiting action exists in pig leucocyte cytosol and that this novel polypeptide is useful as a therapeutic agent for osteoporosis. They named this polypeptide "Elstatin". The present invention was completed based on the above finding.

Accordingly, the present invention provides a polypeptide having an amino acid sequence as shown in Sequence No. 1 in the appended sequence list.

The present invention also provides a cathepsin L-specific inhibitor and a therapeutic agent for osteoporosis which comprises the polypeptide as its active component.

The present invention also provides a pharmaceutical composition comprising an effective amount of the polypeptide and a pharmaceutically acceptable carrier.

The present invention also provides a therapeutic method for osteoporosis characterized by administering an effective amount of the polypeptide.

The present invention also provides use of the polypeptide as a drug.

BRIEF DESCRIPTION OF THE DRAWINGS

FIG. 1 is a graph showing the action of the polypeptide of the present invention with respect to the bone resorption induced by parathyroid hormone.

BEST MODE FOR CARRYING OUT THE PRESENT INVENTION

The polypeptide of the present invention can be isolated, for example, from a cytosol fraction of pig leucocytes by a suitable combination of ion-exchange chromatography, gel filtration, and papain-binding affinity chromatography. Preferably, ion-exchange chromatography, gel filtration, ion-exchange chromatography, and papain-binding affinity chromatography are employed in this order. In this connection, it is preferable to use a DEAE-cellulose column in ion-exchange chromatography, and Sephadex G-50 in gel filtration.

The thus-isolated and purified polypeptide of the present invention has a molecular weight of about 11,768 (calculated based on the amino acid composition and SDS electrophoresis profile), an isoelectric point (pI) of 4.6 and an amino acid sequence as shown in Sequence No. 1.

It suffices that the polypeptide of the present invention comprises 103 amino acid residues shown in Sequence No. 1. The polypeptide may further contain as many as 1 to 10 amino acid residues in the N-terminal part and/or C-terminal part of the sequence.

The polypeptide of the present invention possesses strong cathepsin L-specific inhibitory action and, in addition, strong bone resorption inhibitory action in an in vitro pit formation method, and therefore, is useful as an active component of therapeutic agents for osteoporosis.

The polypeptide of the present invention can be administered as a pharmaceutical composition with a variety of forms prepared according to known methods incorporating pharmaceutically acceptable carriers. In use as therapeutic agents for osteoporosis, the form of the polypeptide is not particularly limited, and forms for oral preparations, injections, suppositories, ointments, and patches may be employed. They can be formulated by conventional manufacture methods which are well known to persons with ordinary skill in the art.

When solid compositions for oral use are prepared, the polypeptide of the present invention is combined with an excipient, and if necessary, a binder, a disintegrator, a lubricant, a colorant, a flavor, a smell corrigent, etc., after which tablets, coated tablets, granules, powders, capsules, and the like are formulated. The above additives can be those generally used in this technical field. Examples of the excipient include lactose, sucrose, sodium chloride, glucose, starch, calcium carbonate, kaolin, microcrystalline cellulose, and silicic acid. Examples of the binder include water, ethanol, propanol, simple syrup, glucose solution, starch solution, gelatin solution, carboxymethylcellulose, hydroxypropylcellulose, hydroxypropyl starch, methylcellulose, ethylcellulose, shellac, calcium phosphate, and polyvinylpyrrolidone. Examples of the disintegrator include dried starch, sodium alginate, agar powder, sodium bicarbonate, calcium carbonate, sodium lauryl sulfate, monoglyceride stearate, and lactose. Examples of the lubricant include purified talc, stearate, borax, and polyethyleneglycol. Examples of the flavor include sucrose, bitter orange peel, citric acid, and tartaric acid.

In order to prepare liquid compositions for oral use, the polypeptide of the present invention is combined with a flavor, a buffer, a stabilizer, a smell corrigent, etc., after which internal liquids, syrups, elixirs, and the like are formulated. In this case, the flavor may be the same as described above. Examples of the buffer include sodium citrate, and examples of the stabilizer include tragacanth, gum arabic, and gelatin.

In order to prepare injection preparations, the polypeptide of the present invention is combined with a pH adjuster, a buffer, a stabilizer, an isotonic agent, a local anesthetic, etc., after which subcutaneous, intramuscular, and intravenous injections are prepared. Examples of the pH adjuster/buffer include sodium citrate, sodium acetate, and sodium phosphate. Examples of the stabilizer include sodium pyrosulfite, EDTA, thioglycollic acid, and thiolactic acid. Examples of the local anesthetic include procaine hydrochloride and lidocaine hydrochloride. Examples of the isotonic agent include sodium chloride and glucose.

In order to prepare suppositories, the polypeptide of the present invention is combined with pharmaceutical carriers known in the art, such as polyethylene glycol, lanolin, cacao butter, fatty triglyceride, and if necessary, a surfactant such as Tween (registered trademark), and then processed by a known method.

In order to prepare ointments, the polypeptide of the present invention is combined with a base, a stabilizer, a lubricant, a preservative, and the like, and thereafter, they are mixed and formulated by a known method. Examples of the base include liquid paraffin, white Vaseline, bleached beeswax, octyldodecyl alcohol, and paraffin. Examples of the preservative include methyl paraoxybenzoate, ethyl paraoxybenzoate, and propyl paraoxybenzoate.

In order to prepare patches, the aforementioned ointments, creams, gels, pastes, and the like are applied to supports therefor which are in common use. Examples of suitable supports include woven or nonwoven materials of cotton, rayon, and chemical fibers, and films and foamed sheets made of soft vinyl chloride, polyethylene, and polyurethane.

The amount of the compound of the present invention to be incorporated into each of the above-described dosage form varies depending on the conditions of the patients to whom the compound is dosed or the form or the like of the compound. Generally, it is preferred that, in a single form of administration, the amount of the compound be from about 1 to 1,000 mg for oral preparation, about 0.1 to 500 mg for injection, and about 5 to 1,000 mg for suppositories. The daily dose of the agent administered in any of the above-described forms varies depending on the conditions of the patient, body weight, age, sex, etc, and therefore, cannot be determined unconditionally. Generally, for adult patients, the daily dose is from about 0.1 to 1,000 mg/kg, and preferably from about 1 to 100 mg/kg once a day or as divided in 2 to 4 times.

EXAMPLES

The present invention will next be described in more detail by way of examples, which should not be construed as limiting the invention thereto.

Example 1

(1) Isolation of leucocytes, cell fractionation and extraction of the protein:

Leucocytes were isolated from pig blood by dextran sedimentation of erythrocytes. In each experiment, 4×1,600 ml of blood was collected in the slaughterhouse immediately after killing the animal. 100 ml of 1% heparin solution in 0.9% NaCl and 400 ml of 6% dextran in Hanks were added to each 1,600 ml of blood. After 30 minutes of standing, the upper layer was removed and centrifuged for 15 minutes at 60×g. To the obtained sediment, a hypotonic solution of 0.32% NaCl containing 4% solution of albumin was added and centrifuged for 15 minutes at 60×g. The cells were further washed with another aliquot of a hypotonic solution of 0.32% NaCl, Hanks buffer, 0.9% NaCl, and 0.34M sucrose, in this order. Subsequently, centrifugation was performed for 15 minutes at 60×g. The cells were resuspended in a sucrose solution, and homogenized in a Teflon homogenizer (20 strokes). The homogenate was then centrifuged for 15 minutes at 60×g. Both the supernatant (leucocyte cytosol) and the sediment (particulate fraction) were combined and centrifuged again for 15 minutes at 8,000×g. The supernatant of the particulate fraction was added to the clear leucocyte cytosol and concentrated by lyophilization.

(2) Polypeptide of the present invention:

The lyophilized sample was dialyzed against 0.05M Tris buffer of pH 7.5 and centrifuged as desired. A clear sample was applied to a DEAE-cellulose column (4×60 cm) and elution was performed using a linear NaCl gradient of 0 to 0.3M. The flow rate was 20 ml/h. Three papain inhibitory peaks were obtained and only the third one (eluted at 0.18M NaCl) was concentrated by lyophilization and further separated on Sephadex G-50 (4.5×120 cm) at a flow rate of 18 ml/h. Inhibitory active fractions were pooled, concentrated and further fractionated on a DEAE-cellulose column (2×40 cm) equilibrated in advance with 0.05M ammonium acetate buffer of pH 6.8. Proteins were eluted with an increasing gradient of NaCl (0 to 0.2M). The final purification of the second inhibitory active peak eluted at 0.025M NaCl was achieved on Cm-papain Sepharose. Non-bound proteins to papain were removed with 0.1M Tris buffer (pH 7.8) containing 0.5M NaCl. Papain-bound proteins were eluted with 0.01M NaOH. The pH of the eluted fractions was immediately adjusted to pH 7.5 with 3M HCl, and the polypeptide of the present invention was obtained.

The amino acid sequence of the polypeptide of the present invention isolated by the above method was determined according to the method described in Biol. Chem., Hoppe-Seyler, Vol. 370, pp. 1147 (1989). The sequence is shown in the attached sequence list as Sequence No. 1. The polypeptide of the present invention was found to have the following properties:

Molecular weight: 11,768 (calculated based on the amino acid composition and SDS electrophoresis profile)

pI: 4.6

Example 2

Enzymatic inhibitory activity:

The inhibitory activity of Elstatin (polypeptide of the present invention) against papain and cathepsin L was measured by the method of Barrett, A. J. and Kirschke, H. described in Method Enzymol., 80, 535–561 (1981) using Bz—DL—Arg-2-naphthylamide or Z—Phe—Arg—MCA as a substrate (Bz, Z and AMC represent benzoyl, benzyloxycarbonyl, and 4-methyl-7-coumarylamide).

The active site of the enzyme was titrated using a cysteine protease inhibitor Ep-475 (L-3-carboxy-trans-2,3-epoxypropyl-leucylamide-(3-guanizino)butane). Papain which had undergone the titration of active site was used to determine the molarity of the inhibitor (Turk, B. et al. J. Biol. Chem. 268, 7323–7329 (1993)).

Equilibrium dissociation constant (Ki) of Elstatin and cathepsin B and H was determined using stopped assay method. In detail, cathepsin B (final concentration: 130 nM) and cathepsin H (final concentration: 25 nM) were incubated together with different concentrations of Elstatin (final concentration: 50–750 nM) in 0.1M phosphate buffer (pH 6.0) containing 2 mM of dithiothreitol and 1.5 mM of EDTA at 25° for 20 minutes. The residual activity was determined using Bz—DL—Arg-2-naphthylamide as a substrate conditions identical to those according to Barrett, A. J. and Kirschke, H. mentioned above. The value Ki was calculated using a method of Henderson (Biochem. J. 127, 321–333 (1972)).

The rate of the reaction employing Z—Phe—Arg—AMC as a substrate was determined by the kinetic analysis of Elstatin, papain, and cathepsin L. Different concentrations of Elstatin and a substrate (papain: 5 μM, cathepsin L: 10 μM) were dissolved in 1.97 ml of a buffer solution described above. In the measurement of cathepsin L, 0.34M acetate buffer (pH 5.5) containing 2 mM dithiothreitol and 1.5 mM EDTA was used. The reaction was started by the addition of 30 μl of activated papain (final concentration: 380 pM) and cathepsin L (final concentration: 60 pM). All the experiments were performed under pseudo-first-order conditions in which Elstatin concentration was at least 10 fold higher than the enzyme concentration. The obtained data were analysed by a non-linear regression analysis of Morrison (Trends Biochem. Sci. 7, 102–105 (1982)).

The enzymatic inhibitory activities obtained by this method are shown in Table 1.

TABLE 1

| Enzymatic Inhibitory Activity | |
|---|---|
| Enzyme | Ki (nM) |
| Papain | 0.19 ± 0.097 |
| Cathepsin B | 335 ± 50 |
| Cathepsin H | 125 ± 7 |
| Cathepsin L | 0.067 ± 0.036 |

From the above results, it is apparent that the polypeptide of the present invention specifically inhibits only cathepsin L among the members of the cathepsin group.

Example 3

Bone resorption inhibitory action:

A method proposed by McSheehy, P. M. J. and Chambers, T. J. in J Clin. Invest., 80, 425–429 (1987) was partly modified and applied.

Unfractionated bone cells were prepared from tibiae, femora and humeri of 1 to 2 day-old Sprague-Dawley rats. The bones were dissected into soft tissues in an ice-cold medium (pH 7.2) [α-minimum essential medium (α-MEM) (Flow Laboratories, McLean, Va.), supplemented with 100 IU/ml of benzylpenicillin] containing 20 mM N-2-hydroxyethyl-piperazine-N'-ethanesulfonic acid (HEPES). In order to prepare a bone cell preparation, long bones were minced with a pair of scissors in the same medium. Subsequently, the cell suspension was triturated with a wide bored plastic pipette. 200 μl of cell suspension ($1\times10^6$ cells/ml) was added to each well of a 96 well-plate containing an ivory slice (thickness: 150 μm, diameter: 6 mm; ultrasonicated and disinfected with 75% ethanol), and the cells were incubated at 37° C. for 2 hours in a $CO_2$ incubator (5% $CO_2$: 95% air). The slices were washed with α-MEM, and transferred to a HEPES-free fresh medium containing 10% FBS, each of test samples of various concentrations and 50 nM of human parathyroid hormone (Peninsula Laboratories Inc., Belmond, Calif.) and incubated for 72 hours. The cells were removed by washing with distilled water vigorously, and then the slices were stained with 0.1% of Toluidine blue for 5 minutes. The total area of pits was measured under a microscope to detect possible osteoclastic bone resorption.

The results are shown in FIG. 1.

FIG. 1 shows that the polypeptide of the present invention has a significantly potent bone resorption inhibitory action.

Preparation Example 1

| Injection liquid: | |
|---|---|
| Polypeptide of the present invention | 5 mg |
| Distilled water for injection | suitable amount |
| In 1 ampule | 5 ml |

An injection liquid was prepared using the above ingredients in the indicated amounts by a routine method.

Preparation Example 2

| Capsules: | |
|---|---|
| Polypeptide of the present invention | 10 mg |
| Lactose | 50 mg |
| Corn Starch | 47 mg |

-continued

| Crystalline cellulose | 50 mg |
|---|---|
| Talc | 2 mg |
| Magnesium stearate | 1 mg |
| In 1 capsule | 160 mg |

Capsules were prepared using the above ingredients in the indicated amounts by a routine method.

Preparation Example 3

| Suppositories: | |
|---|---|
| Polypeptide of the present invention | 20 mg |
| Wittepsol W-35 (registered mark, Dynamite Nobel) | 1,380 mg |
| In 1 piece of suppository | 1,400 mg |

Industrial Utility

Since the polypeptide of the present invention has strong inhibitory action specific to cathepsin L as well as strong bone resorption inhibitory action, it is useful in the treatment of osteoporosis, particularly, senile osteoporosis.

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
    ( A ) LENGTH: 103 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO: 1:

```
MET GLU SER GLU GLU MET LEU ALA GLY GLY LEU THR GLU PRO ARG PRO
 1               5                  10                    15

ALA THR PRO GLU ILE GLN GLU ILE ALA ASN LYS VAL LYS PRO GLN LEU
            20                  25                  30

GLU GLU LYS THR ASN LYS THR TYR GLU LYS PHE GLU ALA ILE ILE TYR
        35                  40                  45

ARG SER GLN VAL VAL ALA GLY THR ASN TYR TYR ILE LYS VAL HIS VAL
    50                  55                  60

GLY GLY ASN ASN TYR VAL HIS ILE ARG VAL PHE GLN SER LEU PRO HIS
65              70                  75                      80

GLN GLU ASP PRO LEU LYS LEU ILE GLY TYR GLN VAL ASP LYS THR LYS
                85                  90                  95

ASP ASP GLU LEU THR GLY PHE
            100         103
```

We claim:

1. An isolated polypeptide having an amino acid sequence represented by Sequence No. 1.

2. A composition for inhibiting cathepsin L comprising an isolated polypeptide having an amino acid sequence represented by Sequence No. 1 as an active ingredient.

3. A therapeutic composition for treating osteoporosis comprising an isolated polypeptide having an amino acid sequence represented by Sequence No. 1 as an active ingredient.

4. A pharmaceutical composition comprising an effective amount of an isolated polypeptide having an amino acid sequence represented by Sequence No. 1 and a pharmaceutically acceptable carrier.

5. A therapeutic method for treating osteoporosis comprising administering to a patient in need of treatment an effective amount of an isolated polypeptide having an amino acid sequence represented by Sequence No. 1.

* * * * *